United States Patent
Yang et al.

(10) Patent No.: US 11,793,822 B2
(45) Date of Patent: Oct. 24, 2023

(54) USES OF PULSATILLA CHINENSIS EXTRACT IN PREPARING DRUG FOR TREATING VIRAL AND/OR BACTERIAL DISEASES

(71) Applicant: SICHUAN INLU WEITE PHARMACEUTICAL TECHNOLOGY CO., LTD., Sichuan (CN)

(72) Inventors: Shilin Yang, Sichuan (CN); Zhetong Su, Sichuan (CN)

(73) Assignee: SICHUAN INLU WEITE PHARMACEUTICAL TECHNOLOGY CO., LTD., Sichuan (CN)

(*) Notice: Subject to any disclaimer, the term of this patent is extended or adjusted under 35 U.S.C. 154(b) by 0 days.

(21) Appl. No.: 17/662,725

(22) Filed: May 10, 2022

(65) Prior Publication Data
US 2022/0273685 A1 Sep. 1, 2022

Related U.S. Application Data

(62) Division of application No. 16/966,855, filed as application No. PCT/CN2019/073239 on Jan. 25, 2019, now abandoned.

(30) Foreign Application Priority Data

Jan. 31, 2018 (CN) .......................... 201810097221.3

(51) Int. Cl.
  A61K 31/704 (2006.01)
  A61P 31/00 (2006.01)
  A61K 9/00 (2006.01)
  A61P 31/12 (2006.01)
  A61P 31/04 (2006.01)

(52) U.S. Cl.
  CPC .......... *A61K 31/704* (2013.01); *A61K 9/0019* (2013.01); *A61P 31/00* (2018.01); *A61P 31/04* (2018.01); *A61P 31/12* (2018.01)

(58) Field of Classification Search
  None
  See application file for complete search history.

(56) References Cited

FOREIGN PATENT DOCUMENTS

| CN | 105535004 A | 5/2016 |
|----|-------------|--------|
| CN | 107137413 A | 9/2017 |
| CN | 107441086 A | 12/2017 |
| CN | 108938654 A | 12/2018 |

OTHER PUBLICATIONS

Xiao, CN 106377537 A, machine translation, Feb. 8, 2017. (Year: 2017).*
Jin, Lan-Mei et al., "Bacteriostatic Test of Body External of the Chinese Herbal Medicine to the Common Pathogenic Bacteria of Milk Cow", Journal of Jinling Institute of Technology, vol. 22, No. 3, Sep. 30, 2006, pp. 95-98, XP009522409, ISSN: 1672-755X, DOI: 10.16515/j.cnki.32-1722/n.2006.03.025.
Haifeng Yang et al., "Antiviral and immunoregulatory role against PCV2 in vivo of Chinese herbal medicinal ingredients", Journal of Veterinary Research, Dec. 27, 2017, vol. 61, No. 4, pp. 405-410.

* cited by examiner

*Primary Examiner* — Layla D Berry
(74) *Attorney, Agent, or Firm* — NKL Law; Allen Xue

(57) ABSTRACT

Use of the compound *Pulsatilla* Saponin B4 represented by formula (I), or a pharmaceutically acceptable salt thereof in the preparation of a medicament for treating viral and/or bacterial diseases, and a medicament comprising the compound *Pulsatilla* Saponin B4 represented by formula (I) or a pharmaceutically acceptable salt thereof as an active ingredient, wherein the disease is dairy cow mastitis.

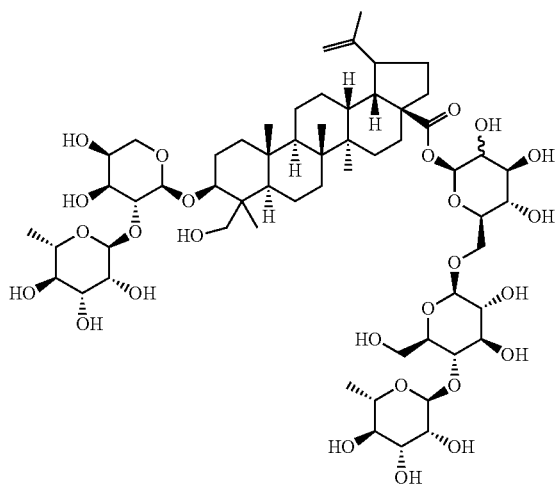

Formula I

9 Claims, 5 Drawing Sheets

| | |
|---|---|
|  |  |
| Day 1, more flocs in the milk | Day 2, the floc became noticeably smaller |
|  |  |
| Day 5, no floc was observed, substantially returned to normal | Day 6, milk was substantially normal |

The milk was thin and contained a small amount of flocs

No floc in milk, yellowish in color

Milk returned to normal, clinically cured

LMT result "++", transferred to the farm housing by veterinarian

| LMT test result of No. 1106021 cow 3 days after the administration, front left "−", rear left "++" | LMT test result of No. 131213 cow 3 days after the administration, rear right "++" |
| LMT test result of No. 131208 cow 3 days after the administration, rear right "+" | LMT test result of No. 0909041 cow 3 days after the administration, rear left "+" |
| LMT test result of No. 532006 cow 3 days after the administration, four udder area "+++" | |

Fig. 5

USES OF PULSATILLA CHINENSIS EXTRACT IN PREPARING DRUG FOR TREATING VIRAL AND/OR BACTERIAL DISEASES

CROSS-REFERENCE TO RELATED APPLICATIONS

This application is a divisional of U.S. patent application Ser. No. 16/966,855, filed Jul. 31, 2020, which is the U.S. national entry of PCT international application no. PCT/CN2019/073239, filed Jan. 25, 2019, which claims the benefit of the priority form Chinese patent application no. 201810097221.3, filed Jan. 31, 2018, the content of which are incorporated herein by reference in their entities.

TECHNICAL FIELD

The present invention relates to the use of *Pulsatilla chinensis* extract in the preparation of a medicament for treating viral and/or bacterial diseases.

BACKGROUND

*Pulsatilla chinensis* (Bge.) Regel is a *Pulsatilla* plant of Ranunculaceae family, and the main medicinal part thereof is its dry roots. The earliest record about *Pulsatilla* is "Shen Nong's Materia Medica". It has a bitter taste, is cool-natured, and returns to the stomach, kidney, and large intestine meridians. The main functions of *Pulsatilia* are detumescence, cooling blood, stopping diarrhea, reducing internal heat, etc. *Pulsatilla* is traditionally used for the treatment of bacterial dysentery, and it also has good therapeutic effects on chill and fever symptoms, swelling and pain of eye. *Pulsatilla* has a variety of pharmacological activities, mainly to improve the body's ability to recognize and resist foreign body invasion, reduce the proliferation rate of tumor cells, reduce the number of pathogenic microorganisms and effectively inhibit the oxidation reaction of free radicals. Among them, the most potential application is in the development of new anti-inflammatory and anti-tumor drugs.

Feng Xiuzhi et al. studied the role of *Pulsatilla* in cell apoptosis and believed that *Pulsatilla* had a good induction effect on gastric cancer cells. In addition, cancer cell proliferation and DNA replication are related to the active ingredients of *Pulsatilla*, which can inhibit the growth of HL260 cells, and inhibit the proliferation of breast cancer cells (MCF-7), lung cancer cells (PG), colon cancer cells (SW480), malignant glioma cells (U87MG) and other tumor cells by inducing apoptosis. Li Wenchao et al. applied *Pulsatilla* alcohol extract to various pathogenic bacteria and studied the antibacterial effect of different solvent extracts. It was found that these extracts all have antibacterial effects, although the effects are different.

Dariy cow mastitis is one of the three major cow diseases recognized in the world. It occurs frequently during lactation. The main reason for its occurrence is pathogenic microbial infection. Other causes include improper milking operations, mechanical damage caused by trauma and damage caused by chemical reagents. Dairy cow mastitis not only affects milk production and causes economic losses, but also affects the quality of milk and harms human health.

Dairy cow mastitis can be divided into two major categories: latent mastitis and clinical mastitis. Clinical mastitis shows obvious clinical symptoms and visible changes in milk, and can be divided into three grades according to the degree of onset: Grade 1: abnormal milk; Grade 2: abnormal milk, the udder becomes hot, painful and enlarged; Grade 3: abnormal milk, the udder becomes hot, painful and enlarged, cows show symptoms of systemic infection. Clinical mastitis is currently the main target of treatment in clinical practice. When cows with clinical mastitis are revealed, isolation treatment is required. Latent mastitis, also known as subclinical mastitis, is the most common type of mastitis in dairy cows. This type of mastitis generally has no clinical symptom, the difference between its milk and normal milk cannot be distinguished by the naked eye, and it needs laboratory reagents to diagnose. In addition, if this type of mastitis does not reach a certain proportion in the herd, it is generally not treated. Because of its concealed incidence, the economic loss caused by latent mastitis to dairy cows is very serious.

At present, the treatment of dairy cow mastitis mostly adopts methods such as udder infusion and intravenous injection, and the therapeutic drugs used are mostly antibiotic drugs, such as cefquinome, enrofloxacin, penicillin, streptomycin and the like. However, long-term use of antibiotics is prone to drug resistance and affects the treatment effect; at the same time, when antibiotics are used for treatment, it is easy to cause antibiotic residues, pollute milk sources, and endanger human health. It is worth noting that if mastitis is a Gram-negative bacterial infection, the use of lactam antibiotics will destroy the cell wall and release endotoxin, causing redness, swelling, heat, and pain in the entire udder area, which will aggravate the condition. Therefore, it is of great significance to find a safe and effective method to treat dairy cow mastitis.

At present, there are no reports on the use of the compounds of the present invention for the treatment of viral and/or bacterial mastitis in dairy cows.

SUMMARY OF THE INVENTION

In order to solve the above technical problem, the present invention provides the use of the compound. *Pulsatilla* Saponin B4 represented by formula I, or a pharmaceutically acceptable salt thereof in the preparation of a medicament for treating viral and/or bacterial diseases:

Formula I

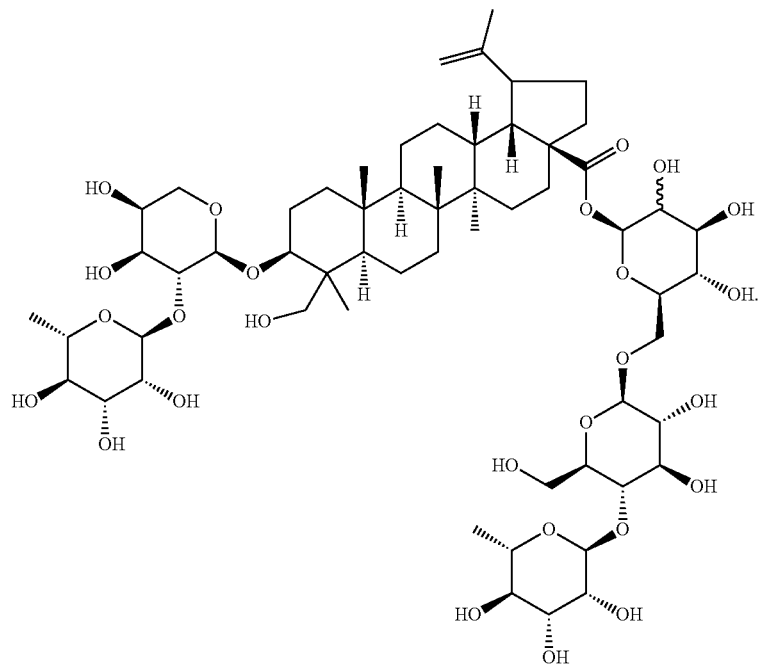

In a further aspect, the medicament is a preparation prepared from the aforementioned compound *Pulsatilla* Saponin B4 or a pharmaceutically acceptable salt thereof as an active ingredient, and pharmaceutically acceptable auxiliary materials.

In a further aspect, the preparation is an injection, an intramammary infusion, powder, ointment, lotion; preferably, the preparation is an injection, an intramammary infusion; more preferably, the preparation is an injection.

In a further aspect, the disease is dairy cow mastitis.

In a further aspect, the dairy cow mastitis is clinical mastitis, latent mastitis.

In a further aspect, the clinical mastitis is clinical mastitis treated for the first time, persistent clinical mastitis, i.e., clinical mastitis that has been treated for a long time but not cured.

The present invention also provides a medicament for treating viral and/or bacterial diseases, which is a preparation prepared from the aforementioned compound *Pulsatilla* Saponin B4 or a pharmaceutically acceptable salt thereof as an active ingredient, and pharmaceutically acceptable auxiliary materials.

In a further aspect, the preparation is an injection, an intramammary infusion, powder, ointment, lotion; preferably, the preparation is an injection, an intramammary infusion; more preferably, the preparation is an injection.

In a further aspect, the disease is dairy cow mastitis.

In a further aspect, the dairy cow mastitis is clinical mastitis, latent mastitis; preferably, the clinical mastitis is clinical mastitis treated for the first time, persistent clinical mastitis.

The *Pulsatilla* extract provided by the present invention is the compound *Pulsatilla* Saponin B4, and its English name is Anemoside B4. Its CAS number is 129741-57-7, molecular formula is $C_{59}H_{96}O_{26}$, molecular weight is 1221.38, and it is a white crystalline powder.

At present, antibiotics are mostly used for the treatment of mastitis. Among them, broad-spectrum sterilization and cell-damaging nucleic acid antibiotics are more commonly used. During the treatment and 4 to 5 days after the treatment, milk needs to be discarded, causing a large economic loss to the farmers and the risk of drug resistance. *Pulsatilla* Saponin B4 is a natural active ingredient extracted from Chinese herbal medicine *Pulsatilla*, is non-toxic and non-drug-resistant. The compound *Pulsatilla* Saponin B4 of the present invention has strong biological activity and has excellent therapeutic effect on dairy cow mastitis. There is no need to discard the milk during the treatment and at the end of the treatment, which not only reduces the economic losses for farmers, but also reduces the risk of drug resistance. In addition, *Pulsatilla* Saponin B4 not only has an excellent therapeutic effect on clinical mastitis, but also has an excellent therapeutic effect on persistent clinical mastitis and latent mastitis. At the same time, *Pulsatilla* saponin injection has the advantages of safety, high efficiency, no residue, no drug resistance, and no toxic and side effects when used in the treatment of dairy cow mastitis.

Obviously, according to the above-mentioned contents of the present invention, in accordance with the ordinary technical knowledge and conventional technical means in the art, various forms of modification, replacement or alteration can be made without departing from the above basic technical idea of the present invention.

The above contents of the present invention will be further described in detail below by way of specific embodiments in the form of examples. However, it should not be construed that the scope of the above subject matter of the present invention is limited to the following examples. All technologies implemented based on the above contents of the present invention belong to the scope of the present invention.

DRAWINGS

FIG. 5 shows the treatment result of cows with latent mastitis.

EMBODIMENTS

Figure 1:
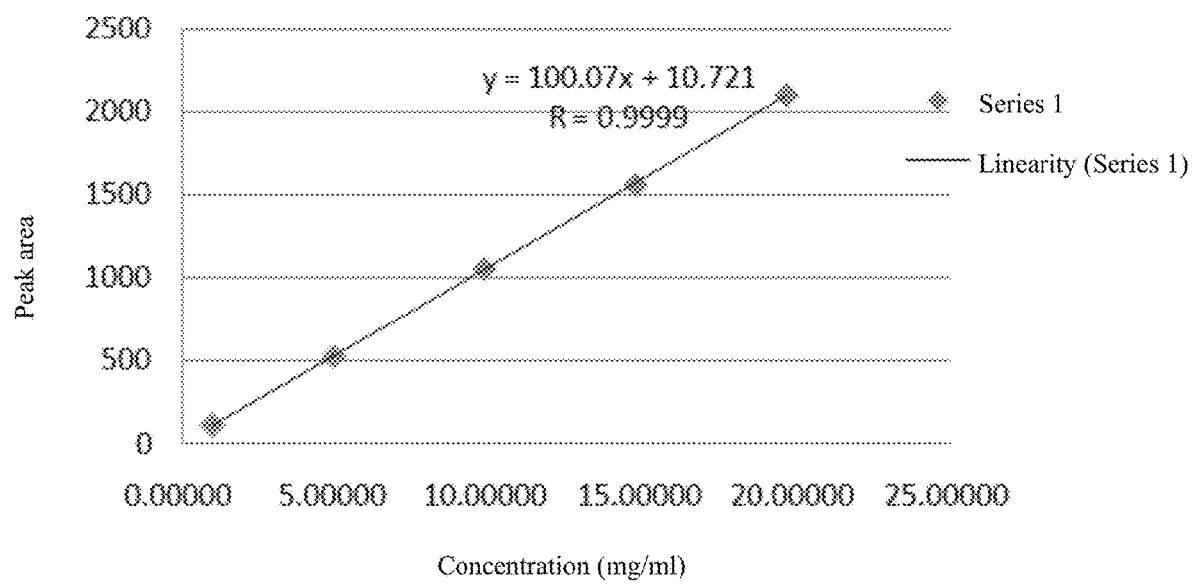
FIG. 1 is a standard curve for *Pulsatilla* Saponin B4 content determination.

Example 1. Preparation of the Compound of the Present Invention

Take 100 kg of *Pulsatilla* medicinal material, add 10 times the amount of 70% ethanol and extract twice by heating and refluxing. The extract is concentrated under reduced pressure at 75° C., centrifuged at 4000 r/min for 10 minutes. The supernatant is passed through a polar macroporous adsorption resin column, and then eluted sequentially with water, 30% ethanol, and 70% ethanol. The fraction eluted with 70% ethanol is concentrated under reduced pressure at 75° C., and then spray-dried to obtain 3450 g of total *Pulsatilla* saponin extract. After dissolving the extract with water and filtering, the filtrate is loaded on a dynamic axial 200 preparative chromatographic system (filled with 10 μm ODS), eluted with 50% methanol, the corresponding eluent is collected according to the chromatographic peak, concentrated under reduced pressure, and freeze-dried to obtain 1700 g of *Pulsatilla* Saponin B4.

Example 2. Content Determination of the Compound of the Present Invention

1. Instruments and Reagents

Agilent 1260 high-performance liquid chromatograph and DAD ultraviolet detector were purchased from Agilent Technologies (China) Co., Ltd., BP211D electronic analytical balance was purchased from Germany Sartorius company, and KQ-400DB numerical control ultrasonic cleaner was purchased from Kunshan Ultrasonic Instrument Co., Ltd.

Sample of *Pulsatilla* Saponin B4, prepared in Example 1.

*Pulsatilla* Saponin B4 reference substance (lot number: 111766-201702, content: 94.7%) was purchased from National Institutes for Food and Drug Control.

2. Chromatographic Conditions

Chromatography column: Sepax Bio-C18 (4.6×250 mm, 5 μm); mobile phase: methanol-water (64:36); detection wavelength: 201 nm; flow rate: 1.0 mL/min.

3. Preparation of Reference Substance Solution

Accurately weigh an appropriate amount of *Pulsatilla* Saponin B4 reference substance, place it into a 10 mL volumetric flask, add mobile phase to dissolve, and bring the volume to the mark to obtain the reference substance solution (containing 1 mg/ml of *Pulsatilla* Saponin B4).

4. Preparation of Sample Solution

Accurately weigh 10 mg sample of *Pulsatilla* Saponin B4 prepared in Example 1, place it into a 10 mL volumetric flask, add mobile phase to dissolve, and bring the volume to the mark to obtain the sample solution.

5. Determination

Accurately measure 20 μL each of the reference solution and the sample solution, inject it into the liquid chromatograph, record the chromatogram, and calculate the content according to the external standard method.

6. Standard Curve and Linear Regression Equation

Take *Pulsatilla* Saponin B4 reference substance, weigh accurately and place it into a 10 mL volumetric flask, add mobile phase to dissolve, bring the volume to the mark to prepare reference substance solutions with concentration of about 1 mg/mL, 5 mg/mL, 10 mg/mL, 15 mg/mL and 20 mg/mL respectively. Accurately measure 20 μL of each solution and inject it into the liquid chromatograph, and record the chromatogram.

TABLE 1

Linear regression equation for content determination of Pulsatilla Saponin B4 reference substance

| Sample | Concentration (mg/mL) | Peak area | Regression equation |
|---|---|---|---|
| 1 | 0.98488 | 115.7 | Y = 100.07 + 10.721 |
| 2 | 4.92440 | 529.5 | R = 0.9999 |
| 3 | 9.84880 | 1057.8 | |
| 4 | 14.77320 | 1560.3 | |
| 5 | 19.69760 | 2097.9 | |

It can be seen from the experimental results that *Pulsatilla* Saponin B4 has a good linear relationship in the concentration range of 1.04-20.80 mg/mL, R=0.9999, and is suitable for the content determination of *Pulsatilla* Saponin B4.

7. Content Determination of *Pulsatilla* Saponin B4 Sample

According to the method described in "3" above, accurately weigh 2 parts of *Pulsatilla*. Saponin B4 reference substance, 10 mg each, place it into a 10 mL volumetric flask, add mobile phase to dissolve, and bring the volume to the mark to obtain Reference solution 1 and Reference solution 2.

According to the method described in "4" above, accurately weigh 2 parts of *Pulsatilla* Saponin B4 sample, 10 mg each, place it into a 10 mL volumetric flask, add mobile phase to dissolve, and bring the volume to the mark to obtain Sample solution 1 and Sample solution 2.

According to the above chromatographic conditions, accurately measure 20 μL of each solution, inject it into the liquid chromatograph, and record the chromatogram.

TABLE 2

Results of content determination of Pulsatilla Saponin B4

| Sample | Weight (mg) | Peak Area | Conc. (mg/mL) | Content (%) | Average content (%) |
|---|---|---|---|---|---|
| Reference solution 1 | 10.22 | 1039.6 1044.4 | 0.968 | // | // |
| Reference solution 2 | 10.05 | 1025.6 1022.5 | 0.952 | // | // |

TABLE 2-continued

Results of content determination of Pulsatilla Saponin B4

| Sample | Weight (mg) | Peak Area | Conc. (mg/mL) | Content (%) | Average content (%) |
|---|---|---|---|---|---|
| Sample solution 1 | 10.13 | 1081.8<br>1092.6 | 1.013 | 99.7 | 99.4 |
| Sample solution 2 | 10.10 | 1075.1<br>1079.2 | 1.010 | 99.1 | |

According to the test results, the content of *Pulsatilla* Saponin B4 obtained in this experiment was 99.4%.

Example 3. Preparation of *Pulsatilla* Saponin B4 Injection

1) Formulation: 1000 mL injection solution made from 50 g *Pulsatilla* saponin B4 with water.
2) Preparation method: Weigh 50 g of *Pulsatilla* Saponin B4 prepared in Example 1, add 800 mL of water for injection to dissolve it completely, filter, adjust pH to 7.0, add water for injection to a volume of 1000 mL, fine filter, fill into a container, seal and sterilize at 100° C. for 30 min.

Example 4. Preparation of *Pulsatilla* Saponin B4 Powder

1) Formulation: 1000 g powder made from 11.000 g of *Pulsatilla* Saponin B4.
2) Preparation method: Weigh 1000 g of *Pulsatilla* Saponin B4 prepared in Example 1, pulverize it into a fine powder, pass through a 100-mesh sieve, and mix well.

Example 5. Preparation of *Pulsatilla* Saponin B4 Intramammary Infusion

1) Formulation: 1000 mL intramammary infusion made from 50 g *Pulsatilla* Saponin B4.
2) Preparation method: Weigh 50 g of Pulsatiha Saponin B4 prepared in Example 1, add 800 mL of distilled water to dissolve it completely, filter, adjust pH to 7.0, add distilled water to a volume of 1000 mL, fine filter, fill into a container, seal, sterilize at 100° C. for 30 min.

The beneficial effects of the present invention will be described below by way of test examples.

Test Example 1. Effects of Different Administration Routes of the Compound of the Present Invention on the Therapeutic Effect of Dairy Cow Mastitis Current administration routes for treating mastitis include udder infusion, intramuscular injection, and intravenous injection.

Among them, udder infusion is the most common route of administration. The therapeutic drugs are directly injected into the affected udder area through the nipple to achieve the effect of local administration and precision therapy. At present, there are a variety of commercial pharmaceutical preparations for udder infusion, such as Aonaikang (澳乃康, Cefquinome Sulfate Intramammary Infusion) by Eastern Along Pharmaceutical Co., Ltd., Ruchang (Cefotifur Injection) by Pfizer, etc.

Intramuscular injection is to inject drugs into the muscle tissue of animals, so that the drugs reach the affected udder area through the blood circulation and exert the therapeutic effect. Intramuscular injection is easy to administer and can control the symptoms of systemic inflammation and fever caused by mastitis to a certain extent.

Intravenous injection is to inject the drug directly into the animal's venous blood, so that the drugs reach the affected udder area through the blood circulation. By intravenous injection, the drug reaches the site of action quickly and can treat systemic symptoms. However, intravenous injection has certain requirements for the properties of the drug, which cannot be a suspension and has little irritation to blood vessels. Bayer (Germany) recommends the treatment of mastitis by intravenous injection of its product Baytrli (Enrofloxacin), which can reach a higher concentration in the affected udder area and exert the therapeutic effect there, and at the same time, can control systemic infections.

The above three routes of administration for treating dairy cow mastitis have their own advantages and disadvantages. This test aims to explore the therapeutic effect of *Pulsatilla* Saponin B4 on dairy cow mastitis and the most suitable route of administration. The results of this study will provide an important reference for how to make *Pulsatilla* Saponin B4 exert the best therapeutic effect, and for future development and packaging of the drug.

1. Test Drugs

*Pulsatilla* Saponin B4 injection prepared in Example 3 at a concentration of 50 mg/mL; *Pulsatilla* Saponin B4 intramammary infusion prepared in Example 5 at a concentration of 50 mg/mL.

Positive control: Cefquinome Sulfate Intramammary Infusion, 8 g/piece (Eastern Along Pharmaceutical Co., Ltd., Nanhai, Foshan).

2. Test Animals 130 sick cows (grade 2 clinical mastitis) were selected and randomly divided into 13 groups with 10 cows in each group.

3. Dosage and Mode of Administration

TABLE 3

Dosage and mode of administration

| Group | Dosage (mL/ affected udder area/ time) | Mode of administration |
|---|---|---|
| Blank control group | Normal saline | / |
| Positive control group | 1 Piece | Intraductal infusion |
| Pulsatilla Saponin B4 injection, intramuscular injection, low-dose group | 10 | Intramuscular injection |
| Pulsatilla Saponin B4 injection, intramuscular injection, medium-dose group | 20 | Intramuscular injection |
| Pulsatilla Saponin B4 injection, intramuscular injection, high-dose group | 30 | Intramuscular injection |
| Pulsatilla Saponin B4 injection, intravenous injection, low-dose group | 40 | Intravenous injection |
| Pulsatilla Saponin B4 injection, intravenous injection, medium-dose group | 60 | Intravenous injection |
| Pulsatilla Saponin B4 injection, intravenous injection, high-dose group | 80 | Intravenous injection |

TABLE 3-continued

Dosage and mode of administration

| Group | Dosage (mL/ affected udder area/ time) | Mode of administration |
|---|---|---|
| Pulsatilla Saponin B4 intramammary infusion, low-dose group | 20 | Intraductal infusion |
| Pulsatilla Saponin B4 intramammary infusion, medium-dose group | 30 | Intraductal infusion |
| Pulsatilla Saponin B4 intramammary infusion, high-dose group | 40 | Intraductal infusion |

Intramuscular injection administration in the affected udder area: *Pulsatilla* Saponin B4 injection is used for local intramuscular injection in the affected udder area, once every morning and evening for 7 days;

Intravenous injection administration: *Pulsatilla* Saponin B4 injection is administered via intravenous injection once a day for 7 days;

Intramammary infusion administration: *Pulsatilla* Saponin B4 intramammary infusion and the positive control (Cefquinome Sulfate Intramammary Infusion) are administered via intraductal infusion in the affected udder area, once every morning and evening for 7 days.

Each administration route of *Pulsatilla* saponin B4 of the present invention is provided with a blank control group, which is administered with normal saline at the same volume.

4. Evaluation Guide

Before each administration, check the cow's body temperature, breathing, mental status, feeding status and other indicators to observe the changes in the udder and milk.

Completely cured: The clinical symptoms such as redness, swelling, heat and pain in the affected udder area disappeared completely, and lactation recovered to normal.

Clinically cured: The clinical symptoms such as redness, swelling, heat, and pain in the affected udder area substantially disappeared, and lactation substantially recovered to normal.

Invalid: No significant improvement or even worsening of clinical symptoms in the affected udder area, or recurrence within two weeks of drug withdrawal, both are considered invalid.

The cure rate is calculated as following:

$$\text{Cure rate} = \frac{\text{number of completely cured cows} + \text{number of clinically cured cows}}{\text{number of cows in experimental group}} \times 100\%$$

5. Results

TABLE 4

Cure rate and cure time of dairy cows mastitis treated via different administration routes

| Group | Cure rate (%) | Cure time |
|---|---|---|
| Blank control group | 0 | / |
| Positive control group | 60 | 5-7 |
| Pulsatilla Saponin B4 injection, intramuscular injection, low-dose group | 50 | 5-7 |
| Pulsatilla Saponin B4 injection, intramuscular injection, medium-dose group | 60 | 5-6 |
| Pulsatilla Saponin B4 injection, intramuscular injection, high-dose group | 80 | 4-6 |
| Pulsatilla Saponin B4 injection, intravenous injection, low-dose group | 40 | 5-7 |
| Pulsatilla Saponin B4 injection, intravenous injection, medium-dose group | 60 | 5-6 |
| Pulsatilla Saponin B4 injection, intravenous injection, high-dose group | 70 | 4-7 |
| Pulsatilla Saponin B4 intramammary infusion, low-dose group | 40 | 6-7 |
| Pulsatilla Saponin B4 intramammary infusion, medium-dose group | 50 | 5-6 |
| Pulsatilla Saponin B4 intramammary infusion, high-dose group | 70 | 4-7 |

The total cure rate and cure time of *Pulsatilla* saponins B4 administrated via different administration routes are shown in Table 4: All the routes of administration have significant effects in the treatment of dairy cow mastitis, and the cure rates of the high-dose group of each route of administration are higher than that of the positive control (Cefquinome Sulfate Intramammary Infusion). Among them, intramuscular injection of *Pulsatilla* Saponin B4 injection has the best healing effect and the shortest treatment period.

Test Example 2. Study of *Pulsatilla* Saponin B4 of the Present Invention in the Treatment of Clinical Mastitis 1. Test Drugs

*Pulsatilla* Saponin B4 injection prepared by the preparation method of Example 3 at a concentration of 50 mg/mL;

Control drug: SHUANGDING injection (双丁注射液) (10 mL/piece, batch number: DV3180701), Hebei Yuanzheng Pharmaceutical Co., Ltd.

2. Test Animals

60 Chinese Holstein cows weighing approximately 612±47 kg, aged 3-5 years old, 2-4 parity, healthy in clinical examination and naturally occurring clinical mastitis during lactation period were selected and randomly divided into 5 groups, 12 in each group.

3. Test Method 3.1 Dosage and Mode of Administration

TABLE 5

Dosage and mode of administration

| Group | Dosage (mL/kg BW) | Mode of administration |
|---|---|---|
| Blank control group | Normal saline | Intramuscular injection |
| Positive drug control group | 0.1 | Intramuscular injection |

TABLE 5-continued

Dosage and mode of administration

| Group | Dosage (mL/kg BW) | Mode of administration |
|---|---|---|
| Pulsatilla Saponin B4 injection, intramuscular injection, low-dose group | 0.025 | Intramuscular injection |
| Pulsatilla Saponin B4 injection, intramuscular injection, medium-dose group | 0.05 | Intramuscular injection |
| Pulsatilla Saponin B4 injection, intramuscular injection, high-dose group | 0.1 | Intramuscular injection |

After the onset of test cows, record the day before administration as D0. Calculate the dosing amount based on body weight according to the pre-designed dosing substance and dosage (Table 5). Starting from the day D1, each group of cows with clinical mastitis was administered the test drug (*Pulsatilla* Saponin B4 injection) or the control drug (SHUANGDING injection) by intramuscular injection, once a day for 4 to 7 days, depending on the cure of the disease. Observe the clinical symptoms of cows in each group before and after administration of the drug (D0~D12), score according to the standard (see Table 6 for details), and make a record of dosing. At the end of the test (D12), based on the observation results of the above indicators, the therapeutic effect on each cow was judged according to the standard, and the cure rate and effective rate of each group of cows were calculated.

3.2 Scoring Standard for Clinical Symptoms of Dairy Cows With Clinical Mastitis At D0 (after the reveal of clinical mastitis, before administration), D1 (after the first administration, before the second administration), D2~D7 (cured cows withdraw drug, and uncured cows continue to receive drug), D8~D12 (all cows withdraw drug), regularly check the clinical symptoms and udder symptoms of each cow, such as mental state, appetite and drinking, etc., and score according to the following table (see Table 6). Record clinical symptoms (local udder symptom score).

TABLE 6

Scoring standard for clinical symptoms of dairy cows with clinical mastitis

| Observations | Score | Scoring standard |
|---|---|---|
| Mental state | 0 | Good |
|  | 1 | Slightly worse |
|  | 2 | Excited or depressed |
|  | 3 | Lying on the floor or even comatose |
| Appetite and drinking | 0 | Strong appetite; moderate drinking |
|  | 1 | Slightly reduced feeding; slightly decreased or increased drinking |
|  | 2 | Significantly reduced feeding; severely decreased or increased drinking |
|  | 3 | Loss of appetite; drink plenty of water or abstain from drinking |
| Lactation capacity | 0 | Normal milk production |
|  | 1 | Reduced milk production |
|  | 2 | Significantly reduced milk production |
|  | 3 | Almost stop lactation |
| Milk traits | 0 | Normal milk traits |
|  | 1 | The milk has a small amount of flakes and clots |
|  | 2 | There is a lot of clot in the milk |
|  | 3 | Milk has traces of blood, pus, and obvious odor |

TABLE 6-continued

Scoring standard for clinical symptoms of dairy cows with clinical mastitis

| Observations | Score | Scoring standard |
|---|---|---|
| Local symptoms of udder | 0 | Normal |
|  | 1 | Mild redness and swelling, no obvious heat pain reaction on palpation |
|  | 2 | Moderate redness and swelling, with heat pain reaction on palpation |
|  | 3 | Severe redness and swelling, obvious heat pain reaction on palpation |

3.3 Detection Method of Somatic Cell Number in Cow Milk

Collect the milk of the cows suffering from clinical mastitis on D0, D7 and D12 of the test, detect and record the number of somatic cells.

3.4 Evaluation of Efficacy

Judging by the clinical symptom examination score

Daily cure rate of treatment on Days 2-7: Starting on D2, if the cow suffering from mastitis meets "the sum of scores <1", the treatment is considered cured. Daily cure rate of treatment on $$\text{Days } 2\text{--}7 = \frac{\text{number of cows cured on Day 2--7}}{\text{number of cows in experimental group}} \times 100\%;$$

the cure rate within 7 days is the sum of the daily cure rate of treatment on Days 2-7.

Daily effective rate of treatment on Days 2-7: Starting on D2, if the cow suffering from mastitis meets "≤1 the sum of scores≤2", the treatment is considered effective. Daily effective rate of treatment on $$\text{Days } 2\text{--}7 = \frac{\text{number of cows effectively treated on Day 2--7}}{\text{number of cows in experimental group}} \times 100\%;$$

the effective rate within 7 days is the sum of the daily effective rate of treatment on Days 2-7.

Recurrence rate: During the period from D5 to D12, if the diseased cow judged as successfully treated meets "the sum of scores>2" after withdrawal of the drug, it is regarded as recurrence.

$$\text{Recurrance rate} = \frac{\text{number of cows recurred after successfully treated}}{\text{number of cows successfully treated}} \times 100\%.$$

Cure rate of treatment on Day 12 (total cure rate): On D12, if the cow suffering from mastitis meets "the sum of scores <1", it is regarded as cured on Day 12. The cure rate on $$\text{Day } 12 = \frac{\text{number of cows cured on Day 12}}{\text{number of cows in experimental group}} \times 100\%.$$

Effective rate of treatment on Day 12 (total effective rate): On D12, if the cow suffering from mastitis meets "1≤the sum of the scores≤2", the treatment is considered effective. The effective rate on $$\text{Day } 12 = \frac{\text{number of cows effectively treated on Day 12}}{\text{number of cows in experimental group}} \times 100\%.$$

With the cure rate as the main indicator, and the effectiveness, clinical symptom score, and somatic cell number as the secondary indicators, comprehensively evaluate the therapeutic effect of the test drug (*Pulsatilla* Saponin B4 injection) on clinical mastitis of naturally infected cows, and compare it with the therapeutic effect of the control drug (SHUANGDING Injection) to determine the clinical recommended dosage of the tested drug.

4. Test Results

4.1 Results of Treatment of Cows With Clinical Mastitis in Each Group

It can be seen from Table 7 that when using *Pulsatilla* Saponin B4 injection to treat clinical mastitis in dairy cows, regardless of the low-, medium- and high-dose, the cure rate in 7 days and the total cure rate are higher than that of the control group using SHUANGDING Injection, and the average cure time is shorter than the control group, indicating that *Pulsatilla* Saponin B4 injection is superior to SHUANGDING injection in the treatment of clinical mastitis. The total cure rate of the high-dose group is higher than those of the medium- and low-dose groups. The total cure rate of the medium-dose group is the same as that of the low-dose group, but there is no recurrence, and the average cure time is shorter than that of the low-dose group, showing a certain dose-effect relationship.

TABLE 7

Results of therapeutic effects of cows with clinical mastitis in each group

| Group | Cure rate in 7 days | Recurrence rate | Total cure rate | Total effective rate | Average cure time |
|---|---|---|---|---|---|
| Low-dose group | 83.33% | 8.33% | 75.00% | 100% | 6.33 days |
| Medium-dose group | 66.67% | 0 | 75.00% | 100% | 6.11 days |
| High-dose group | 75.00% | 0 | 91.67% | 100% | 6.91 days |
| Control group | 41.67% | 0 | 58.33% | 66.67% | 7.00 days |

4.2 Clinical Symptom Examination Score of Dairy Cows With Mastitis in Each Group It can be seen from Table 8 that the clinical symptom examination score of dairy cows with mastitis in low-dose group was not significantly different between D0-D4 and between D5-D12 ($p>0.05$), but was significantly different between D5-D12 and D0-D2, between D7-D12 and D0-D4 ($p<0.05$), indicating that in low-dose group, cows with mastitis improved significantly at D5, and cured significantly at D7. The clinical symptom examination score of dairy cows with mastitis in medium-dose group was not significantly different between D0-D1, between D2-D5, and between D4-D12 ($p>0.05$), but was significantly different between D3-D12 and D0-D2, between D6-D12 and D0-D3 ($p<0.05$), indicating that in medium-dose group, cows improved significantly at D3, and cured significantly at D6. The clinical symptom examination score of dairy cows with mastitis in high-dose group was not significantly different between D0-D3, between D1-D5, between D3-D6, and between D7-D12 ($p>0.05$), but was significantly different between D4-D12 and D0, between D6-D12 and D0-D2, and between D7-D12 and D0-D6 ($p<0.05$), indicating that in high-dose group, cows with mastitis generally started to improve at D4, the number of cured cows has increased significantly at D6, and some cows cured at D7. The clinical symptom examination score of dairy cows with mastitis in control group was not significantly different between D0-D4, between D2-D6, and between D3-D12 ($p>0.05$), but was significantly different between D5-D12 and D0-D4, and between D7-D12 and D0-D6 ($p<0.05$), indicating that in control group, cows improved at D5, and a certain number of cows cured at D7.

The clinical symptom examination score of medium-dose group at D0 was significantly higher than those of the low-dose group and high-dose group ($p<0.05$), indicating that the disease of cows in the medium-dose group was more serious; the clinical symptom examination score of medium-dose group at D1 was significantly higher than the other 3 groups ($p<0.05$), the clinical symptom examination score of medium-dose group at D2 was significantly higher than those of the low-dose group and high-dose group ($p<0.05$), indicating that in the early stage of treatment, the medium-dose group has an obvious effect on improving the clinical symptoms of cows with mastitis; the differences in the clinical symptom examination score of cows between the four groups at D3-D5 and D7 were not significant ($p>0.05$); the clinical symptom examination score of the cows in the control group at D12 was significantly higher than that of the high-dose group ($p<0.05$), indicating that the therapeutic effect of the control group is inferior to that of the *Pulsatilla* treatment group.

TABLE 8

Clinical symptom examination score of dairy cows in each group

| G | N | D 0 | D 1 | D 2 | D 3 | D 4 | D 5 | D 6 | D 7 | D 12 |
|---|---|---|---|---|---|---|---|---|---|---|
| L | 1 | 1.58 ± | 1.42 ± | 1.17 ± | 1.08 ± | 1.08 ± | 0.83 ± | 0.83 ± | 0.33 ± | 0.50 ± |
|   | 2 | $0.67^A_B$ | $0.51^A_B$ | $0.58^{AB}_B$ | $0.29^{AB}_A$ | $0.29^{AB}_A$ | $0.58^{BC}_A$ | $0.83^{BC}_{AB}$ | $0.89^C_A$ | $1.00^C_{AB}$ |
| M | 1 | 2.92 ± | 2.67 ± | 2.17 ± | 1.42 ± | 1.08 ± | 1.00 ± | 0.50 ± | 0.33 ± | 0.25 ± |
|   | 2 | $2.11^A_A$ | $1.61^A_A$ | $1.11^{AB}_A$ | $0.90^B_A$ | $0.67^{BC}_A$ | $0.74^{BC}_A$ | $0.52^C_B$ | $0.49^C_A$ | $0.45^C_{AB}$ |
| H | 1 | 1.50 ± | 1.33 ± | 1.42 ± | 1.17 ± | 1.00 ± | 1.00 ± | 0.83 ± | 0.33 ± | 0.08 ± |
|   | 2 | $0.67^A_B$ | $0.65^{AB}_B$ | $0.67^{AB}_B$ | $0.58^{ABC}_A$ | $0.43^{BC}_A$ | $0.60^{BC}_A$ | $0.58^C_{AB}$ | $0.65^D_A$ | $0.29^D_B$ |

TABLE 8-continued

Clinical symptom examination score of dairy cows in each group

| G | N | D 0 | D 1 | D 2 | D 3 | D 4 | D 5 | D 6 | D 7 | D 12 |
|---|---|-----|-----|-----|-----|-----|-----|-----|-----|------|
| C | 12 | 2.08 ± 0.67$^A_{AB}$ | 1.83 ± 0.72$^{AB}_B$ | 1.75 ± 0.75$^{AB}_{AB}$ | 1.50 ± 0.67$^{ABC}_A$ | 1.42 ± 0.90$^{ABC}_A$ | 1.33 ± 0.78$^{BC}_A$ | 1.17 ± 0.83$^{BC}_A$ | 0.92 ± 1.00$^C_A$ | 0.92 ± 1.24$^C_A$ |

Note:
"G" means "Group",
"N" means "Number of cattle",
"L" means "Low-dose group",
"M" means "Medium-dose group",
"H" means "High-dose group";
"C" means "Control group";

and

In the same line, superscripts with different capital letters indicate significant differences ($p<0.05$), and superscripts with the same capital letters indicate no significant differences ($p>0.05$); in the same column, subscripts with different capital letters indicate significant differences ($p<0.05$), and subscripts with the same capital letters indicate no significant differences ($p>0.05$). The same applies to the table below.

4.3 Somatic Cell Detection Results of Cow Milk in Each Group

TABLE 9

Somatic cell detection results of milk from cured cows in each group ($10^4$/mL)

| Group | Number of cattle | D0 | D7 | D12 |
|-------|------------------|-----|-----|-----|
| Low-dose group | 9 | 255.8 ± 38.9$^A_A$ | 90.5 ± 55.8$^B_{AB}$ | 47.5 ± 35.6$^B_{AB}$ |
| Medium-dose group | 9 | 244.6 ± 42.0$^A_A$ | 65.8 ± 51.5$^B_B$ | 38.1 ± 23.0$^B_B$ |
| High-dose group | 11 | 310.6 ± 132.4$^A_A$ | 182.3 ± 151.7$^B_A$ | 48.8 ± 58.9$^C_{AB}$ |
| Control group | 7 | 267.9 ± 123.7$^A_A$ | 180.7 ± 119.2$^A_A$ | 88.8 ± 67.4$^B_A$ |

It can be seen from Table 9 that the somatic cells in the milk of cows in each group showed a downward trend at D0-D7. The difference between D7 and D12 in the low-dose group, medium-dose group and control group was not significant, but D7 was significantly different from D0, indicating that with the treatment of the drug, milk somatic cell improved significantly at D7 and did not relapse afterwards. In the high-dose group, D0, D7, and D12 were all significantly different, which on the one hand showed a significant improvement in milk somatic cells, and on the other hand was also related to the longer average cure time of the cows in this group. The difference in milk somatic cells of the four groups of cows at D0 was not significant, indicating that from the perspective of milk somatic cells, the cows in each group had similar disease status at the time of onset. At D7, the milk somatic cells of the medium-dose group cows were significantly lower than those of the high-dose group and the control group, which was related to the shorter average cure time of the medium-dose group. At D12, the milk somatic cells of the cows in the control group were significantly higher than that of the medium-dose group, indicating that the therapeutic effect of *Pulsatilla* Saponin B4 injection on dairy cow mastitis is better than SHUANGDING Injection.

From the therapeutic effect of *Pulsatilla* Saponin B4 injection on clinical mastitis of dairy cows, the number of milk somatic cells, clinical cure rate and cure test observations, it can be seen that all *Pulsatilla* Saponin B4 injections with different concentrations have obvious therapeutic effect on dairy cow clinical mastitis, and the effect is better than the positive control SHUANGDING Injection. In addition, *Pulsatilla* Saponin B4 injection is non-toxic and non-drug-resistant, and there is no need to discard the milk during the treatment and at the end of the treatment, which not only reduces the economic losses for farmers, but also reduces the risk of drug resistance.

Figure 2:
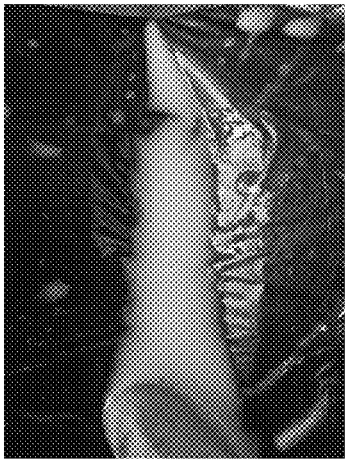
FIG. 2 is a comparison of milk of cows suffering from clinical mastitis before and after treatment with *Pulsatilla* Saponin B4 injection.
Figure 2:
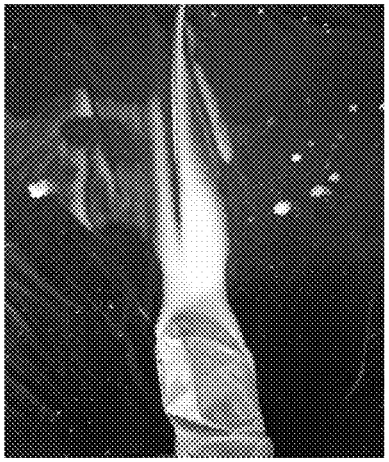
Figure 2:
Figure 2:
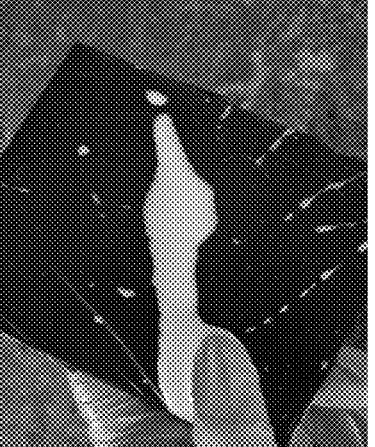
Figure 3:
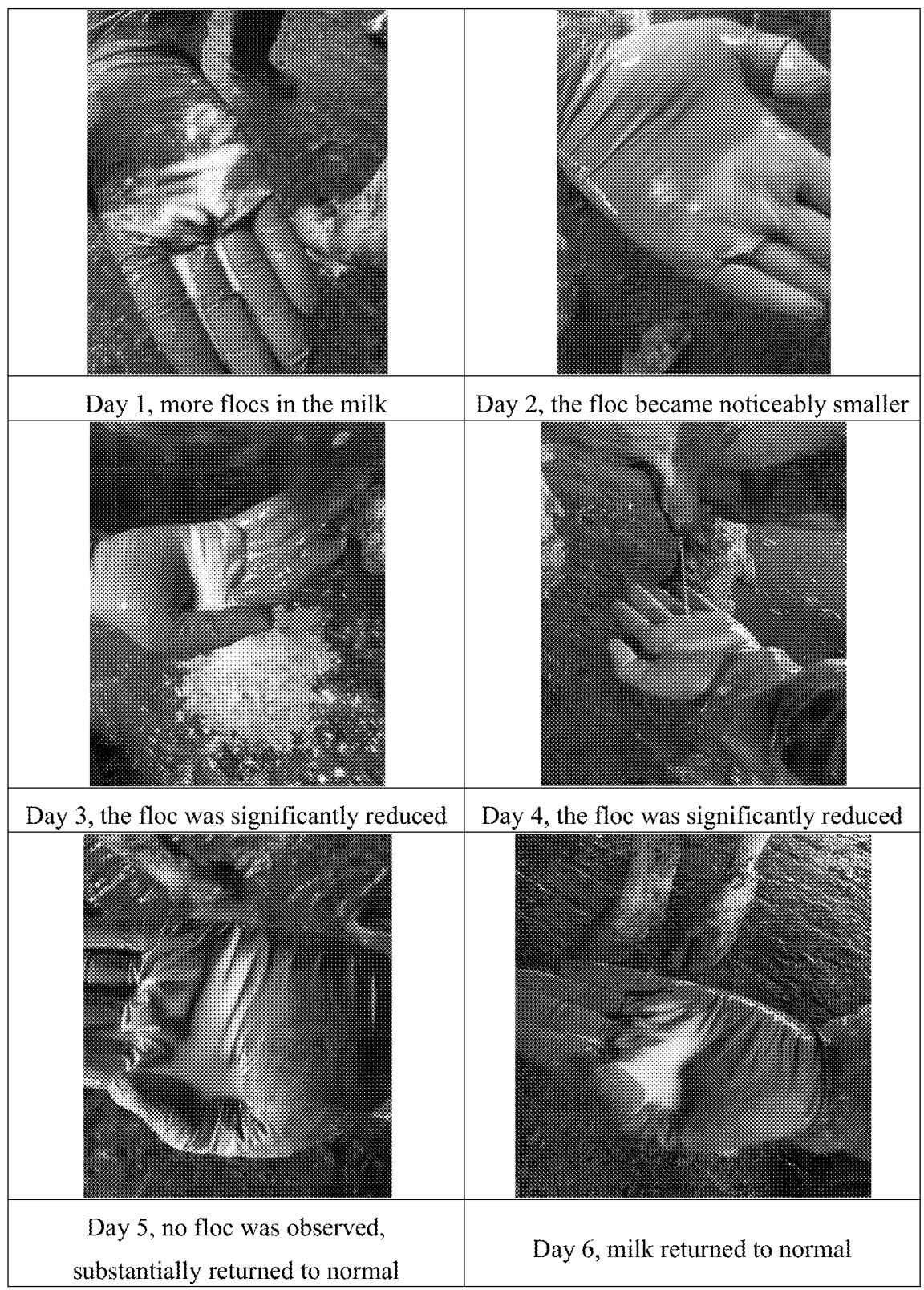
FIG. 3 is a comparison of milk of cows suffering from clinical mastitis before and after treatment with *Pulsatilla* Saponin B4 injection.

FIGS. 2 and 3 show the comparison of milk of cows with clinical mastitis before and after treatment with *Pulsatilla* Saponin B4 injection. As can be seen from FIG. 2 and FIG. 3, on the first day of treatment, the cows with clinical mastitis had more flocs in the milk. As the treatment time increases, the flocs gradually decreased, and the milk gradually returned to normal. After the sixth day of treatment, the milk returned to normal. It showed that *Pulsatilla* Saponin B4 injection has a significant effect in treating clinical mastitis and improving milk quality.

Test Example 3. Study of *Pulsatilla* Saponin B4 of the Present Invention in the Treatment of Persistent Clinical Mastitis and Latent Mastitis 1. Test Drugs

*Pulsatilla* Saponin B4 injection prepared by the preparation method of Example 3 at a concentration of 50 mg/mL;

2. Test Cows

The test selected 8 existing cows suffering from clinical mastitis in the dairy farm of Shijiazhuang Tianquan Dairy Cows Co., Ltd. These 8 cows have been treated for about a month but have not been cured (2 of them were close to dry, i.e., almost no milk was produced). These 8 cows have been treated by farm veterinarians, the treatment drugs and methods include udder infusing Cefquinome Sulfate Intramammary Infusion, intravenous injecting cephalosporins injection, and gavage with Gongying San (公英散), etc.

The test randomly selected 6 cows with latent mastitis in Tianquan dairy farm, all of which had at least one udder area of "++" or above in the last LMT test by the veterinarian.

3. Test Contents

To study the effect of *Pulsatilla* Saponin B4 injection on persistent clinical mastitis and the effect of *Pulsatilla* Saponin B4 injection on latent mastitis.

4. Test Drugs, Dosage and Mode of Administration

In the test, the *Pulsatilla* Saponin B4 injection prepared by the preparation method of Example 3 was used to treat 6 cows with persistent clinical mastitis and 2 cows with persistent clinical mastitis and close to dry. No matter how many udder areas were inflamed, intramuscular injection (60 mL) was taken once a day.

For 6 randomly selected cows with latent mastitis, no matter how many udder areas were inflamed, intramuscular injection (30 mL) was taken once a day.

TABLE 10

Test drugs, dosage and mode of administration

| Test cow | Number of cattle | Injection volume | Mode of administration |
| --- | --- | --- | --- |
| Persistent clinical mastitis | 6 | 60 mL | Intramuscular injection, once a day |
| Close to dry | 2 | 60 mL | Intramuscular injection, once a day |
| Latent mastitis | 6 | 30 mL | Intramuscular injection, once a day |
| Total | 15 | // | Intramuscular injection, once a day |

5. Test Results

5.1 Treatment Result of Cows With Persistent Clinical Mastitis

In the test, 8 cows with clinical mastitis and have not been cured for a long time were selected and treated. After 3 administrations, four cows were cured, one cow improved significantly, and one cow showed no significant effect; it was not effective for two cows close to dry. The results of the study showed that *Pulsatilla* Saponin B4 has good effects on dairy cow mastitis for which treatment with antibiotics or other means are ineffective.

Treatment results for some cows that have not been cured for a long time: For the cow with an ear-tag numbered 8558, the milk of the cow before treatment was thin and contained a small amount of flocs, and the LMT test result was "+++"; after intramuscular injection of 60 mL *Pulsatilla* Saponin B4 injection once, there was no visible flocs in the milk, and the color of the milk was slightly yellow. After the second administration, milk returned to normal, and the result of LMT test by the veterinarian was "++". Then the cow was transferred to the farm housing by the veterinarian.

Figure 4:
FIG. 4 shows the treatment result of No. 8558, a cow that has been treated for a long time but not cured.
Figure 4:
Figure 4:
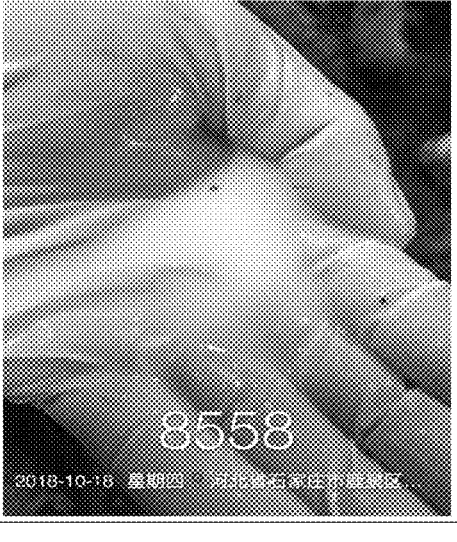
Figure 4:
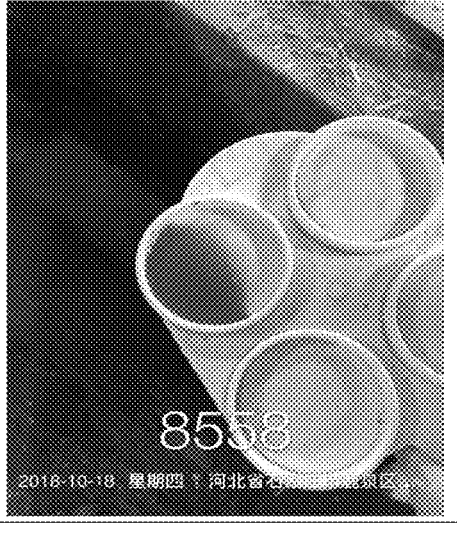

FIG. 4 shows the treatment of the cow numbered 8558, which has not been cured for a long time. It can be seen from FIG. 4 that as the treatment time increases, the milk secretion of the cow numbered 8558 gradually became normal. After 2 times of administration, the milk returned to normal, the cow was clinically cured.

5.2 Treatment of Cows With Latent Mastitis

According to the LMT test results of farm veterinarian, 6 cows with latent mastitis were randomly selected, all of which had at least one udder area of "++" or above. *Pulsatilla* Saponin B4 injection 30 mL was administrated via Intramuscular injection. Three days later, the LMT test results of 5 cows improved significantly. The improvement of the other cow (No. 532006) was not significant, but no aggravation occurred.

TABLE 11

Test results of latent mastitis

| Ear-tag number | Last LMT result | Somatic cells before the test | LMT results three days after administration |
| --- | --- | --- | --- |
| 131213 | Both front right and rear right+++ | 1323 | Front right−, rear right++ |
| 0909041 | Rear left++, front right+++ | 1294 | Rear left+, front right− |
| 131208 | Front right+++, rear right++ | 847 | Front right−, rear right+ |
| 160128 | Four udder areas+++ | 5450 | Four udder areas++ |
| 532006 | Four udder areas+++ | 2041 | Four udder areas+++ |
| 1106021 | Front left++, rear left+++ | — | Front left−, rear left++ |

Note:
Since there is no somatic cell detector in the farm, the test needs to be performed in other farms. The veterinarian of the dairy farm has not completed the somatic cell testing, but the LMT test results after three days of administration showed significant improvement in 5 cows with latent mastitis.

Remarks on special cows: For cow No. 1106021, before administration, two udder areas on the left suffered from latent mastitis, the LMT test results of front left and rear left were "++" and "+++" respectively; rear right was completely dry and no milk can be squeezed out; the milk of the first three squeezing of front right was thick and yellow in color, and after squeezing out a few more, bloody mucus-like fluid without milk characteristics appeared. Intramuscular injecting *Pulsatilla* Saponin B4 injection 30 mL once a day, and after 3 days of administration, there was no improvement in the front right, the LMT test results of front left and rear left were "−" and "++" respectively, somatic cells were significantly reduced, and the effect was significant.

The other 5 cows suffering from latent mastitis were injected intramuscularly once a day with Saponin B4 injection 30 mL. After three days of treatment, 4 cows improved and the results of LMT showed that the somatic cells were reduced; the improvement of the other cow (No. 532006) was not significant. FIG. 5 shows the treatment results of some cows suffering from latent mastitis after three days of treatment with *Pulsatilla* Saponin B4 injection. It can be seen from FIG. 5 that the condition of cows suffering from latent mastitis improved after administration of medication.

The results of the study showed that *Pulsatilla* Saponin B4 has a good effect on latent mastitis.

The diseased cows have been treated by farm veterinarians via udder infusing Cefquinome Sulfate Intramammary Infusion, intravenous injecting cephalosporins injection, and gavage with Gongying San (公英散) for about a month, but the treatment was ineffective, and the disease was then turned into chronic mastitis, which was manifested by thin milk and continuous floc in the milk. The reason for the above situation may be: first, the variety of drug used in the farm for the treatment of mastitis was simplex, only antibacterial drug was used in the treatment process without paying attention to anti-inflammatory; second, the variety of antibiotics used was simplex, and the pathogenic bacteria were not isolated and identified, resulting in bacterial resistance and insensitivity to drugs; third, long-term treatment leads to hyperplasia of mammary tissue, causing chronic inflammation, which in turn makes it more difficult for the drug to reach the effective site, making the condition stubborn. When *Pulsatilla* Saponin B4 injection was used to treat 8 cows recruited in the test, after 3 administrations, four cows were cured, one cow improved significantly, and one cow showed no significant effect; it was not effective for two cows close to dry. The results of the study showed that *Pulsatilla* Saponin B4 has a good effect on dairy cow mastitis for which treatment with antibiotics or other means are ineffective.

Latent mastitis is one of the most common types of mastitis in dairy cows. This type of mastitis generally has no clinical symptom, the difference between its milk and normal milk cannot be distinguished by the naked eye, and it needs laboratory reagents to diagnose. If this type of mastitis does not reach a certain proportion in the herd, it is generally not treated. Because of its concealed incidence, the economic loss caused by latent mastitis to dairy cows is very serious. When *Pulsatilla* Saponin B4 injection was used to treat 6 cows suffering from latent mastitis, four cows improved; one cow showed significant effect and reduced somatic cells in the LMT test; one cow had no significant improvement. The results of the study showed that *Pulsatilla* Saponin B4 has a good effect on latent mastitis.

In addition, during the treatment of dairy cow mastitis, randomly selected the tested *Pulsatilla* Saponin B4 injection and entrusted the Sichuan Provincial Veterinary Drug Inspection Institute to conduct more than 200 antibiotic tests, and no antibiotic component was detected. On the second day after the administration to dairy cows, all milk can pass the antibiotic residue test conducted on the farm. *Pulsatilla* Saponin B4 has little effect on the immunoglobulin and inflammatory factors in the cow milk, thus can ensure the stability of the milk composition. In addition, since there is no residue, it will not affect the quality of fresh milk in dairy farms.

At present, antibiotics are mostly used for the treatment of mastitis. Among them, broad-spectrum sterilization and cell-damaging nucleic acid antibiotics are more commonly used. During the treatment and 4 to 5 days after the treatment, milk needs to be discarded, causing a large economic loss to the farmers and the risk of drug resistance. *Pulsatilla* Saponin B4 is a natural active ingredient extracted from Chinese herbal medicine *Pulsatilla*, is non-toxic and non-drug-resistant. The compound *Pulsatilla* Saponin B4 of the present invention has strong biological activity and has excellent therapeutic effect on dairy cow mastitis. There is no need to discard the milk during the treatment and at the end of the treatment, which not only reduces the economic losses for farmers, but also reduces the risk of drug resistance. In addition, *Pulsatilla* Saponin B4 not only has an excellent therapeutic effect on clinical mastitis, but also has an excellent therapeutic effect on persistent clinical mastitis and latent mastitis. At the same time, *Pulsatilla* saponin injection has the advantages of safety, high efficiency, no residue, no drug resistance, and no toxic and side effects when used in the treatment of dairy cow mastitis.

The invention claimed is:

1. A method for treating a viral disease or a bacterial disease, comprising administering an effective amount of a composition to a subject in need thereof, wherein the composition comprises *Pulsatilla* Saponin B4 of Formula I:

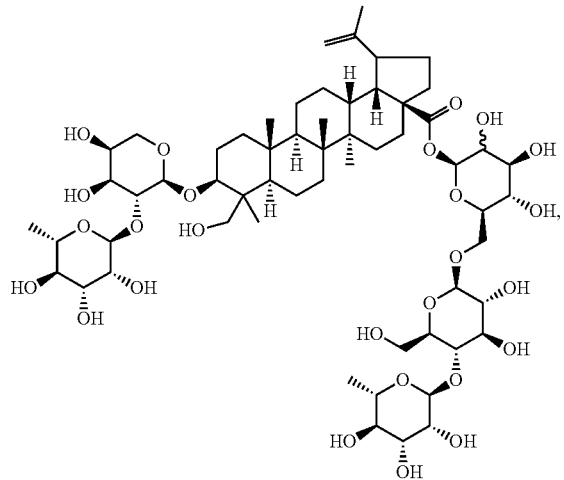

Formula I or a pharmaceutically acceptable salt thereof, and pharmaceutically acceptable auxiliary materials, wherein the disease is dairy cow mastitis.

2. The method of claim 1, wherein the dairy cow mastitis is clinical mastitis or latent mastitis.

3. The method of claim 2, wherein the clinical mastitis is clinical mastitis treated for the first time.

4. The method of claim 2, wherein the clinical mastitis is persistent clinical mastitis.

5. The method of claim 1, wherein the composition is administered through injection.

6. The method of claim 5, wherein the composition comprises a concentration of 50 mg/mL of *Pulsatilla* Saponin B4 of Formula I.

7. The method of claim 5, wherein the composition is administered through intramuscular injection or intravenous injection.

8. The method of claim 1, wherein the composition is administered through intramammary infusion.

9. The method of claim 8, wherein the composition comprises a concentration of 50 mg/mL of *Pulsatilla* Saponin B4 of Formula I.

* * * * *